(12) United States Patent
Andersen et al.

(10) Patent No.: US 12,702,789 B2
(45) Date of Patent: Aug. 11, 2026

(54) METHOD FOR FORMING A URINARY CATHETER TIP

(71) Applicant: Coloplast A/S, Humlebaek (DK)

(72) Inventors: Birger Andersen, Birkeroed (DK); Jakob Oeelund, Alleroed (DK)

(73) Assignee: Coloplast A/S, Humlebaek (DK)

( * ) Notice: Subject to any disclaimer, the term of this patent is extended or adjusted under 35 U.S.C. 154(b) by 451 days.

(21) Appl. No.: 18/568,406

(22) PCT Filed: Jun. 17, 2022

(86) PCT No.: PCT/DK2022/050132
§ 371 (c)(1),
(2) Date: Dec. 8, 2023

(87) PCT Pub. No.: WO2022/262923
PCT Pub. Date: Dec. 22, 2022

(65) Prior Publication Data

US 2024/0285898 A1 Aug. 29, 2024

(30) Foreign Application Priority Data

Jun. 17, 2021 (DK) ........................... PA 2021 70308

(51) Int. Cl.
*A61M 25/00* (2006.01)

(52) U.S. Cl.
CPC ....... *A61M 25/001* (2013.01); *A61M 25/0017* (2013.01); *A61M 2207/10* (2013.01); *A61M 2210/1089* (2013.01)

(58) Field of Classification Search
CPC ............ A61M 25/001; A61M 25/0017; A61M 2207/10; A61M 2210/1089; A61M 25/0009; B29C 48/002; B29C 48/0022
USPC .................................................. 264/150, 151
See application file for complete search history.

(56) References Cited

U.S. PATENT DOCUMENTS

| | | | | |
|---|---|---|---|---|
| 4,551,292 | A | 11/1985 | Fletcher et al. | |
| 5,547,364 | A | 8/1996 | Wong et al. | |
| 5,780,073 | A | 7/1998 | Chen et al. | |
| 5,985,195 | A | 11/1999 | Muskatello | |
| 2003/0135200 | A1 | 7/2003 | Byrne | |
| 2005/0171591 | A1 | 8/2005 | McHale et al. | |
| 2007/0016168 | A1 * | 1/2007 | Conway | A61L 29/14 264/678 |
| 2009/0171320 | A1 * | 7/2009 | Yoshifusa | A61M 25/0043 604/528 |
| 2011/0146680 | A1 * | 6/2011 | Conway | A61L 29/16 128/207.14 |
| 2015/0174364 | A1 | 6/2015 | Kennelly et al. | |

(Continued)

FOREIGN PATENT DOCUMENTS

| | | | |
|---|---|---|---|
| EP | 0354695 | A2 | 2/1990 |
| WO | 1996026825 | A1 | 9/1996 |

(Continued)

*Primary Examiner* — Sarang Afzali
*Assistant Examiner* — Darrell C Ford
(74) *Attorney, Agent, or Firm* — Coloplast Corp., Coloplast A/S; Nick Baumann

(57) ABSTRACT

A method for forming a urinary catheter tip on a tubular object is provided. Further methods of forming two tips positioned head-to-head are also provided. Methods for forming a urinary catheter is provided. A urinary catheter having a flex-tip and obtained by the methods is provided.

15 Claims, 6 Drawing Sheets

(56) References Cited

U.S. PATENT DOCUMENTS

2015/0297863 A1 10/2015 Hannon et al.
2015/0352321 A1 12/2015 Hannon et al.
2017/0035989 A1* 2/2017 Gilman ............. B29C 45/14426
2018/0015248 A1 1/2018 Logan et al.
2019/0262579 A1* 8/2019 Lovmar ............ A61M 25/0017
2020/0269011 A1* 8/2020 Carlsson ........... A61M 25/0015

FOREIGN PATENT DOCUMENTS

WO 2015160492 A1 10/2015
WO 2016206701 A1 12/2016

* cited by examiner

METHOD FOR FORMING A URINARY CATHETER TIP

The invention relates to methods for forming a urinary catheter tip, methods for manufacturing a urinary catheter and a urinary catheter obtained by the methods.

BRIEF DESCRIPTION OF THE DRAWING

The accompanying drawings are included to provide a further understanding of embodiments and are incorporated into and a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

FIGS. 1A-1C illustrate the steps in a longitudinal cross-sectional view and FIG. 2 illustrate the same steps in a perspective view.

FIG. 3 illustrates the entire corrugator and FIG. 4 illustrates a detail of the corrugator with a tubular object, on which a urinary catheter tip is to be formed.

DETAILED DESCRIPTION

Figure 1A:
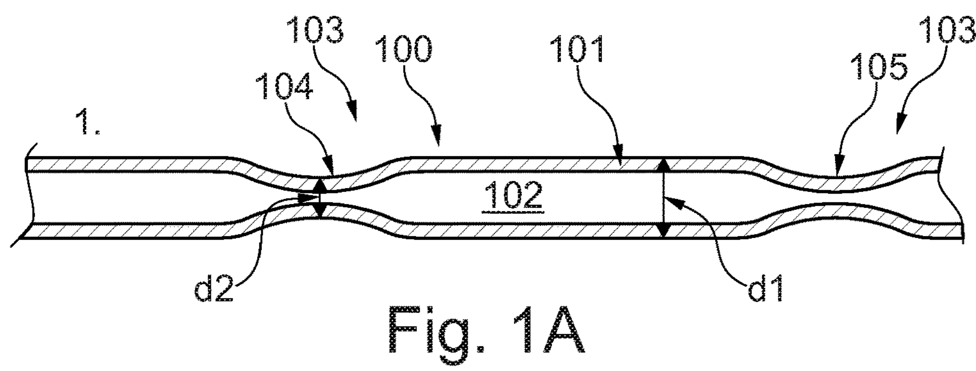
FIGS. 1A-1C and 2 illustrate steps in a method of forming a urinary catheter tip, when it is processed in a method as described herein.

Embodiments relate to a method for forming a urinary catheter tip on a tubular object comprising the steps of

- Providing a tubular object made from polymeric plastic material,
- Forming an indentation in the tubular object by using a shaping tool having a protrusion,
- Cutting the tubular object at a first predetermined distance proximally of the indentation,
- Heating and shaping the proximal end of the tubular object to form a urinary catheter tip at the proximal end of the tubular object.

Embodiments relate to a method for making a urinary catheter comprising the steps of

- Providing a tubular object made from polymeric plastic material,
- Forming an indentation in the tubular object by using a shaping tool having a protrusion,
- Cutting the tubular object at a first predetermined distance proximally of the indentation,
- Cutting the tubular object at a second predetermined distance distally of the indentation,
- Heating and shaping the proximal end of the tubular object to form a urinary catheter tip at the proximal end of the tubular object,
- Providing eyelets in the tubular object distally of the indentation,
- Providing a connector or handle in the distal end.

A method as described above allows for an easy manufacturing of a urinary catheter tip, in particular a so-called flex-tip (se detailed description below). Another method as described above allows for an easy manufacturing of a urinary catheter, in particular a urinary catheter with a so-called flex-tip.

In the following, whenever referring to a proximal end of an element of the invention, the referral is to the end adapted for insertion. Whenever referring to the distal end of an element, the referral is to the end opposite the insertion end. In other words, the proximal end is the end closest to the user, when the catheter is to be inserted and the distal end is the opposite end—the end furthest away from the user when the catheter is to be inserted.

The longitudinal direction is the direction from the distal to the proximal end. The transverse direction is the direction perpendicular to the longitudinal direction, which corresponds to the direction across the tubular object or the catheter.

The tubular object as described may be extruded to a transverse dimension and wall thickness suitable for use as an intermittent urinary catheter.

Usually, intermittent urinary catheters are from size 8 FR (CH8) to size 18 FR (CH18). FR (or French size or Charriere (CH)) is a standard gauge for catheters approximately corresponding to the outer circumference in mm. More accurately, the outer diameter of the catheter in mm corresponds to FR divided by 3. Thus, CH8 corresponds to a catheter with an outer diameter of 2.7 mm and CH18 corresponds to a catheter with an outer diameter of 6 mm. The most common sizes are size CH10, CH12 and CH14 for males and size CH8, CH10 and CH12 for females.

The wall thickness of a urinary catheter is typically between 0.3 and 1.0 mm.

The tip-forming process of a urinary catheter as described above relates to forming a tip portion, which consists of, from a proximal end, a rounded spherical or olive shaped bulb followed by a necked portion, which necked portion transitions into a tubular portion. Such a tip portion is sometimes referred to as a flex-tip because the proximal portion (the bulb) has an ability to flex with respect to the tubular portion due to the necked portion in between. The tubular portion has a first exterior diameter corresponding to the CH-size and an inner lumen extending from the proximal end throughout the tubular portion to the distal end. The bulb may have a third exterior diameter that is either larger than, equal to, or smaller than the first exterior diameter of the tubular portion. The necked portion has a second exterior diameter, which is smaller than the first exterior diameter of the tubular portion and the third exterior diameter of the bulb.

The bulb may be hollow, because only the proximal end is rounded off in the mould, thus leaving a hollow bulb. However, during this moulding process, the bulb may also be melted to a degree, such that it is solid.

To avoid that the necked portion gets too flexible, this necked portion has at least a partly closed cross-section meaning that at least a portion of the necked portion is solid.

The indentation is made such that the length of the indentation is between 10 and 30 mm and the transverse diameter of the tubular object at the necked portion is between 2 and 3 mm. This is done by providing a portion of the belt with a protrusion extending radially outwards from the belt of the corrugator.

The finished urinary catheter is provided with eyelets or drainage openings in a proximal portion of the tubular portion (i.e. just distally of the necked portion). The eyelets or drainage openings are configured for allowing urine from the bladder to drain into the inner lumen and through the inner lumen to the distal end of the finished urinary catheter.

Furthermore, the finished urinary catheter may be provided with a connector in the distal end, which allows connection of the catheter to a drainage tube. The finished urinary catheter may also be provided with a handle in the distal end.

For a male catheter, the length of the finished urinary catheter is between 35 and 40 cm and for a female catheter, the length is between 5.5 and 12 cm, for example between 7 and 8 cm, such as 7.7 cm.

The tubular object may be provided by extrusion. In this case, the shaping tool may be positioned immediately following the extruder in the manufacturing line. By doing this, the material of the tubular object is already heated and further heating for shaping purposes can be avoided. However, the tubular object may also be made by injection moulding and then entered into the shaping tool and heated during the process of shaping.

Various shaping tools may be used in the context of this disclosure. All of the shaping tools have driving wheels positioned at a transverse distance between them.

In some examples, the shaping tools may be heated. It depends on the material of the tubular object, which is to be processed in the method as described herein. It also depends on whether the material is already heated, for example as a result of an extrusion process, prior to being put into contact with the shaping tools. If the material is not heated, then the shaping tools have to be heated to a temperature allowing the material of the tubular object to be softened.

In an example, the material may be thermoplastic Polyurethane (TPU), which requires a processing temperature between 120 and 220° C. In another example, the material may be thermoplastic Polyethylene, which requires a processing temperature of between 80 and 200° C. If the tubular object is extruded immediately prior to being shaped by the shaping tools, then the shaping tools will not have to be heated. On the contrary, cooling may have to be applied to the shaping process, e.g. in the form of air-cooling or liquid-cooling. Cooling assists in preventing deformation of the product during shaping.

In some examples, the driving wheels are directly equipped with shaping elements configured for providing the indentation in tubular objects as disclosed herein. The driving wheels may also themselves be at least partly formed so as to be able to provide indentations in tubular objects. Furthermore, the driving wheels may drive corrugator belts as described in the following.

A corrugator comprises two opposing belts each having a number of shaping elements, which can be positioned in varying distances with respect to the lengthwise direction. The belts are driven by driving wheels, typically two per belt, positioned a distance apart in the lengthwise direction. In a radial direction, the shaping elements have one or more protrusions extending radially outwards from the belt and towards the opposing belt. Two opposing protrusions will typically be provided at the same lengthwise position, so that the corrugator belts are lengthwise symmetrical along an axis extending between the two belts.

However, the shaping elements and protrusions need not be positioned symmetrically along a lengthwise extending axis. There may be instances where it is advantageous that the protrusions are positioned asymmetrically, for example, if a urinary catheter with a so-called coudé tip or Tiemann tip is to be made using this technique. A coudé tip or Tiemann tip is a term typically used for tips that are bent at an angle with respect to the longitudinal direction of the tubular portion.

The shaping elements may be made of 10-50 mm blocks, typically made of aluminium or stainless steel.

The shaping and heating to form the proximal bulb may be done in a mould. This may be a simple half-spherical mould, into which, the proximal end of the unfinished tip is inserted. The mould may be heated to assist in rounding off the proximal end. By rounding off is meant to provide the proximal end with a half spherical or olive shaped bulb.

The first predetermined distance mentioned above may by approximately 1 cm. This means that the tubular object is cut approximately 1 cm proximally of the indentation. This will leave enough material to form the proximal bulb by moulding as described above.

The second predetermined distance mentioned above may be either between 35 and 50 cm for male urinary catheters or between 8 and 18 cm for female urinary catheters.

Embodiments relate to a method for forming two urinary catheter tips on a tubular object comprising the steps of

- Providing a tubular object made from polymeric plastic material,
- Forming in sequence: a first bulb indentation, a bulb, a break-indicator, a second bulb and a second indentation in the tubular object by using a shaping tool having protrusions; the first and second indentation being spaced apart by a third predetermined distance,
- Cutting the break-indicator so as to separate the two urinary catheter tips from each other.

Embodiments relate to a method for forming two urinary catheter tips on a tubular object comprising the steps of

- Providing a tubular object made from polymeric plastic material,
- Forming in sequence: a first indentation, a first bulb, a break-indicator, a second bulb and a second indentation in the tubular object by using a shaping tool having protrusions; the first and second indentation being spaced apart by a third predetermined distance,
- Pulling the two ends of tubular object in opposite directions, so as to separate the two urinary catheter tips from each other by breaking the break-indicator.

Either of the embodiments for forming two urinary catheter tips may be followed by steps of modifying the first and second bulbs so as to provide a smooth, atraumatic proximal end of a urinary catheter. This modifying may be done by forming in a mould, by grinding, by smoothing or otherwise. However, in embodiments, no finishing step is required, because the material itself will contract to a smooth finish during cooling. This is a characteristic in thermoplastic polymer materials, which are contemplated to be used in the described processes.

Examples relate to the third predetermined distance being between 20 mm and 30 mm.

Examples relate to the break-indicator having a transverse dimension of between 0.01 mm—or even thinner—and 1 mm. The lengthwise dimension may be between 0.5. and 5 mm. The break-indicator is configured to break under a low stress. Thus, depending on the type of material, the break-indicator has to be so thin that it is easy to break. By easy to break is meant that the break-indicator will break under a longitudinally applied force of 20 N.

Examples relate to the tubular object being extruded prior to being shaped by the shaping tool. In related examples, the extrusion of the tubular object is done immediately prior to the shaping with the shaping tool, such that the shaping step occurs within approximately 3 seconds following the extrusion.

Providing an extrusion process immediately prior to the shaping alleviates the need for heating the shaping tool. As mentioned above, cooling may be provided, if the shaping step occurs shortly following the extrusion.

Examples relate to the shaping tool being heated to a temperature of between 50° C. and 160° C.

Examples relate to the shaping tool being in the form of two rotatable wheels positioned such that a peripheral edge of the rotatable wheels comes into contact with an exterior surface of the tubular object, where each of the rotatable wheels is provided with the protrusion configured for forming the indentation in the tubular object.

The centre of rotation of the rotatable wheel will be positioned displaced with respect to the longitudinal direction of the tubular object. This means that when the rotatable wheel rotates, it will rotate in the same plane as the tubular object is forwarded. Therefore, a peripheral edge of the rotatable wheel will come into contact with a sidewall of the tubular object and thus be able to make an indentation. It may be possible to use only one rotatable wheel, but advantageously, two rotatable wheels positioned opposite each other on either side of the tubular object are used.

In an example, the circumference of the rotatable wheel corresponds to the length of the catheter, such that the wheel rotates one revolution, when the tubular object travels a distance corresponding to the length of the catheter. In this example, the rotatable wheel will only be provided with one protrusion corresponding to the indentation, which is to be made in the tubular object.

In another example, the circumference of the rotatable wheel corresponds to twice the length of the catheter, such that when the wheel rotates one revolution, the tubular object travels a distance corresponding to two lengths of the catheter. In this example, the rotatable wheel will be provided with two protrusions corresponding to the indentations, which are to be made in the tubular object, i.e. in two catheter lengths.

In an embodiment, the shaping tool is an un-symmetrical rotatable wheel. It may, for example, be a plate having a shape as a part of a circle. The un-symmetrical rotatable wheel can be positioned and used in the same way as a rotatable wheel described above. In examples, the un-symmetrical rotatable wheel may be provided with two parts of a circle positioned directly opposite from each other with respect to the centre point of the wheel. In this way, the wheel will rotate one revolution, when the tubular object travels a distance corresponding to the length of two catheter lengths.

In embodiments, two shaping tools are positioned on either side in a lengthwise direction, so as to allow for providing two indentations with a third predetermined distance between them. Thereby, it will be possible to provide two urinary catheter tips as described above.

In an embodiment, the shaping tool is a corrugator. The corrugator may have a length corresponding to the length of the catheter or it may be shorter. The corrugator will have shaping elements comprising a cavity corresponding to the tubular object as well as protrusions configured for providing the indentation in the tubular object.

Examples relate to the shaping elements of the corrugator being moved with a speed of 3-10 m/min, even though faster speeds such as up to 20 m/min may be contemplated.

The speed and the length of the corrugator is correlated such that the tubular object needs time to set following shaping, while being in the corrugator. By setting is meant that the tip formed on the tubular object keeps it shape. This means that the faster the corrugator runs, the longer it has to be to allow the shaped tubular object to set inside the corrugator. If the corrugator runs rather slow, then the corrugator can be shorter and still allow the tip to set inside the corrugator.

Examples relate to the corrugator being heated by electrical heating. The corrugator may be heated to a temperature of between 50° C. and 160° C.

Examples relate to the shaping elements of the corrugator being made of a material selected from the group of steel and aluminium.

Examples relate to the shaping tool being positioned at a distance of between 0 and 10 cm from the extruder.

Examples relate to the shaping tool being positioned between 10 and 20 cm from the extruder. In these examples, there will be room for a pre-heating device to heat the tubular object prior to entering the tubular object into the corrugator.

DETAILED DESCRIPTION OF THE DRAWING

FIG. 1A discloses an endless tubular object 100, which is obtained by an extrusion process. The extruder is not shown in FIG. 1A but is contemplated to be positioned to the right of the tubular object, such that the process direction is from right to left. An extruder is well-known in the art and will not be described further.

The distal direction is defined as the direction towards the extruder and the proximal direction is defined as the direction away from the extruder. The tubular object is seen in cross-section in a longitudinal direction. The tubular object has a wall 101 which encloses an inner lumen 102. A first diameter d1 of the tubular object is indicated in FIG. 1.

FIG. 1A also illustrates that the tubular object 100 has been indented at lengthwise spaced positions 103. These indentations 104, 105, define a length of a finished catheter tube between two consecutive indentations, as will be described in the following. A smallest diameter at the indentation is indicated as d2. The indentations 104, 105 follow a curved shape, such as a circular arc, a hyperbolic arc or an elliptical arc.

Figure 1B:
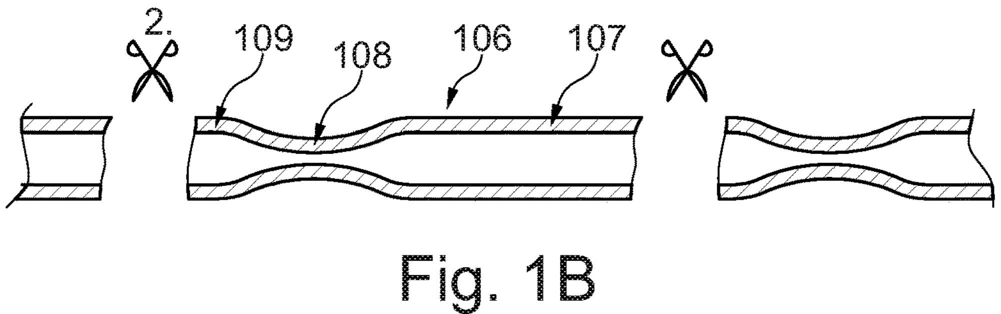

FIG. 1B illustrates that the tubular object 100 is cut approximately 1 cm proximally of the position of the smallest diameter of the indentations 104, 105. This leaves a segmented object 106 consisting of, from a distal direction, a longer tubular part 107, a necked part 108 at an indentation and a short tubular part 109 at the proximal portion.

Figure 1C:
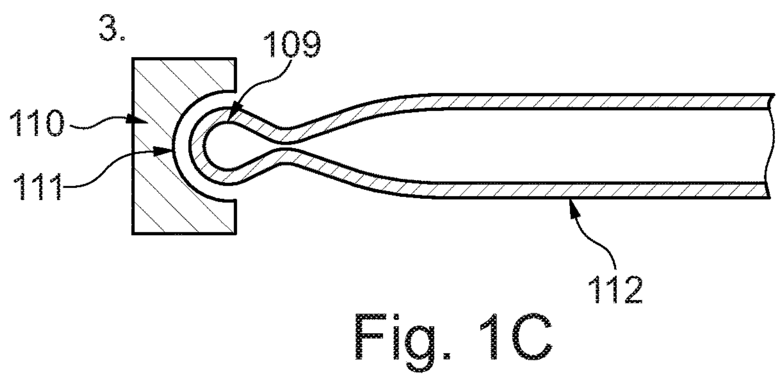

FIG. 1C illustrates that following the cutting, the short tubular part 109 is tip-formed using a heated mould 110 with a cavity 111 to close it off completely at the proximal end. This is a well-known technique usually used for making nelaton-tipped catheters but is in this process used to close off a flex-tip. The tip-formed tubular object 112 thus obtained may subsequently have eyelets cut and be provided with a connector, and optionally coated to obtain a finished catheter.

Figure 2:
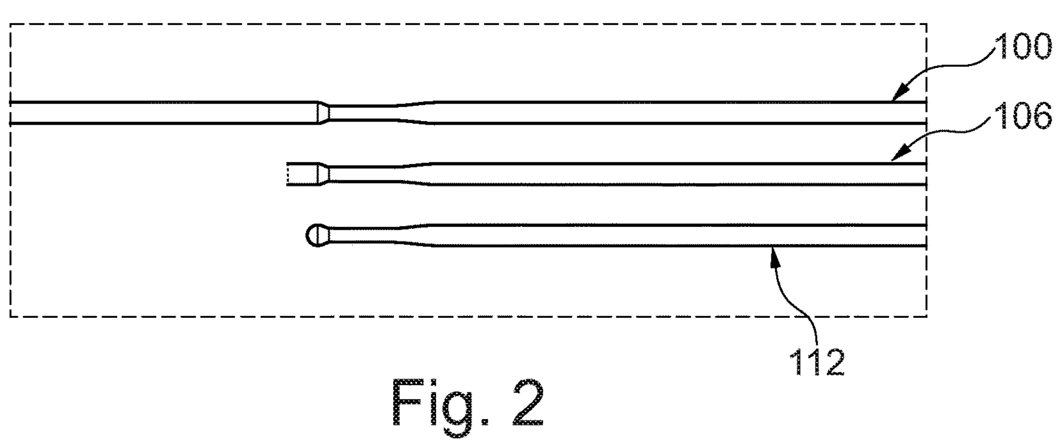

FIG. 2 illustrates, in a perspective view, three steps in the process, the tubular object 100 at the top, the segmented object 106 in the middle and the tip-formed tubular object 112 at the bottom.

Figure 3:
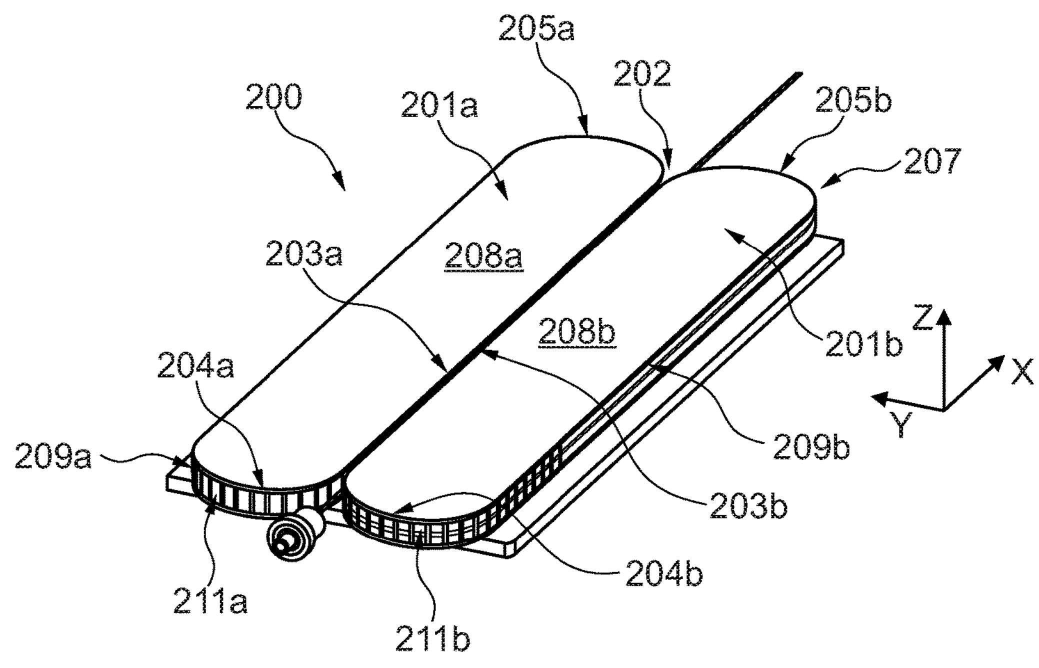
FIGS. 3 and 4 illustrate perspective views of a corrugator, which can be used in a method of forming a urinary catheter tip.

FIG. 3 illustrates a corrugator that may be used in the described manufacturing process. The corrugator 200 consists of two forming parts 201*a*, 201*b*, which are positioned with a small clearance 202 between them. Each of the forming parts 201*a*, 201*b* is shown in FIG. 3 as being of a rectangular shape with rounded corners, when seen from the top, so that a side 203*a*, 203*b* of each forming part faces each other. The sides 203*a*, 203*b* facing each other extend from one end 204*a*, 204*b*, to another opposite end 205*a*, 205*b* of the forming parts. The direction between the one end 204*a*, 204*b* and the opposite end 205*a*, 205*b* defines the longitudinal direction of the corrugator and forming parts. A three-dimensional coordinate system may be used to describe the directions, and in this case, the longitudinal direction corresponds to a direction of the X-axis. An outwardly facing side 206*a*, 206*b*, completes the rectangular shape. All corners 207 are rounded so as to allow an endless belt to travel around an edge of the forming parts as explained below.

A top-surface 208*a*, 208*b* of each forming part faces upward and from this top-surface, the forming part 201*a*, 201*b* extends towards the floor leaving a side edge 209*a*, 209*b* extending all the way around the forming parts 201*a*, 201*b*. In the three-dimension coordinate system, the top-surface will be in the XY-plane. The side edges will extend in the Z-direction.

In the side edge 209*a*, 209*b*, a groove 210*a*, 210*b*, is provided. This groove 210*a*, 210*b* leaves room for an endless belt 211*a*, 211*b* extending all the way around the edges 209*a*, 209*b*. The endless belts 211*a*, 211*b* are driven by driving wheels (not visible in FIG. 3) positioned at end portions 212*a*, 212*b* close to the end 204*a*, 204*b* and opposite end portions 213*a*, 213*b* close to the end 205*a*, 205*b*.

The tubular object is entered into the corrugator at the end 204*a*, 204*b* and moved along the corrugator to exit at end 205*a*, 205*b*.

Figure 4:
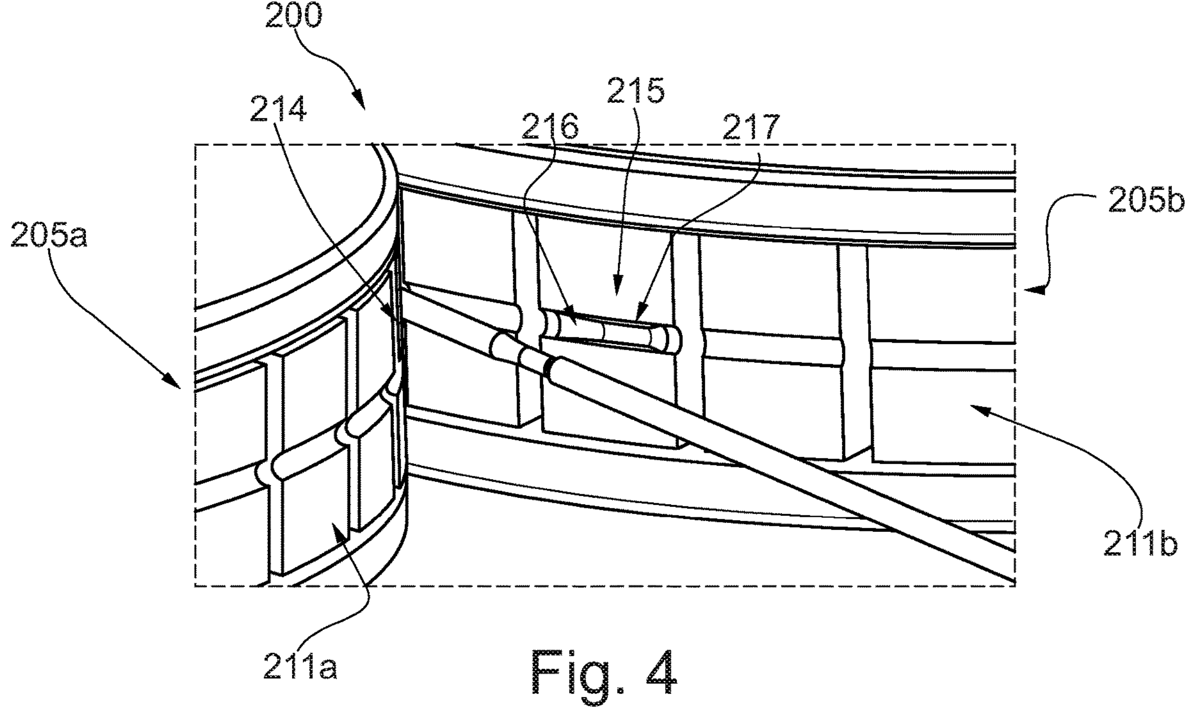

FIG. 4 illustrates a detail of the corrugator 200, of the end 205*a*, 205*b*, where the tubular object exits the corrugator. As can be seen from the figure, the endless belts 211*a*, 211*b* comprise a number of shaping elements 214 and 215. Each of the shaping elements 214 comprises a groove 216 configured for refining the outer surface of a tubular object. In one of the shaping elements 215, the groove comprises a protrusion 217 configured for providing the indentation in the tubular object; the indentation is illustrated for example in FIG. 1A. In FIG. 4, the shaping element 215 comprising a protrusion 217 can only be seen to the right in the figure, however, the shaping element positioned directly across from this indentation forming shaping element will also comprise a protrusion in the groove, so that the indentation becomes circumferential around the tubular object. In this way, a tubular object having a necked portion as illustrated in FIG. 2 is provided.

Figure 5:
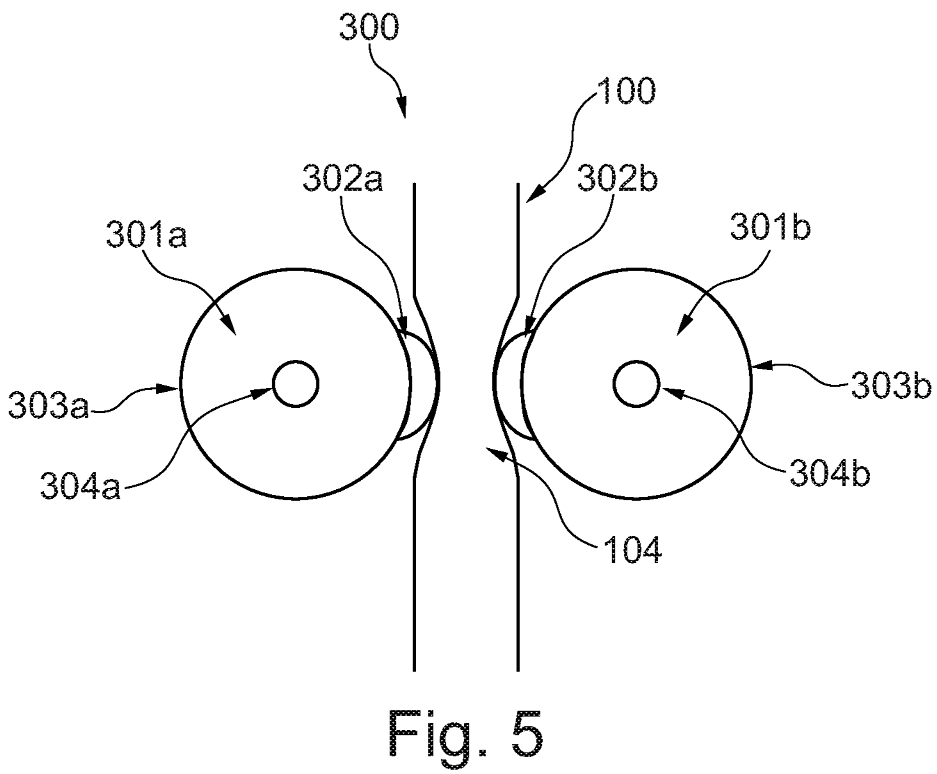
FIG. 5 illustrate a top view of a rotatable wheel, which can be used in a method as described herein.

FIG. 5 illustrate a top view of a rotatable wheel system 300, which can be used in a method of manufacturing as described herein. In the figure, the two rotatable wheels 301*a*, 301*b* are shown, with a portion of the tubular object 100 between them. Each of the rotatable wheels 301*a*, 301*b* is provided with a shaping element 302*a*, 302*b*, positioned at a periphery 303*a*, 303*b* of the rotatable wheels. The wheels are mounted on driving wheels 304*a*, 304*b*, such that a centre of the rotatable wheels is mounted on the driving wheels 304*a*, 304*b*. From the figure, it can be seen that contact between the shaping elements 302*a*, 302*b* provides the indentation 104 in the tubular object.

Figure 6:
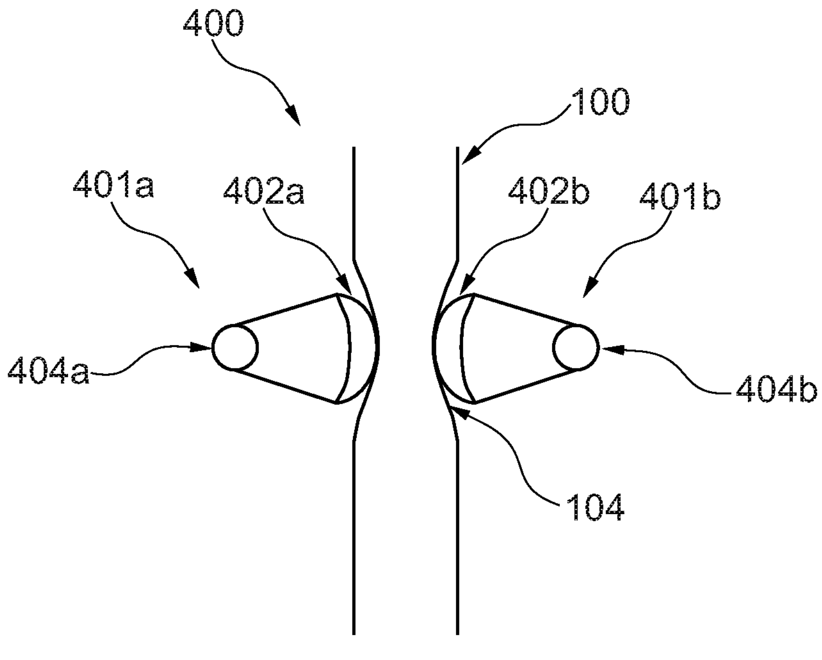
FIG. 6 illustrate a top view of an un-symmetrical rotatable wheel, which can be used in a method as described herein.

FIG. 6 illustrates a top view of an un-symmetrical rotatable wheel system 400, which can be used in a method of manufacturing as described herein. In the figure, the two un-symmetrical rotatable wheels 401*a*, 401*b* are shown, with a portion of the tubular object 100 between them. Each of the rotatable wheels 401*a*, 401*b* is provided with a shaping element 402*a*, 402*b*. The wheels are mounted on driving wheels 404*a*, 404*b*. From the figure, it can be seen that contact between the shaping elements 402*a*, 402*b* provides the indentation 104 in the tubular object.

Figure 7:
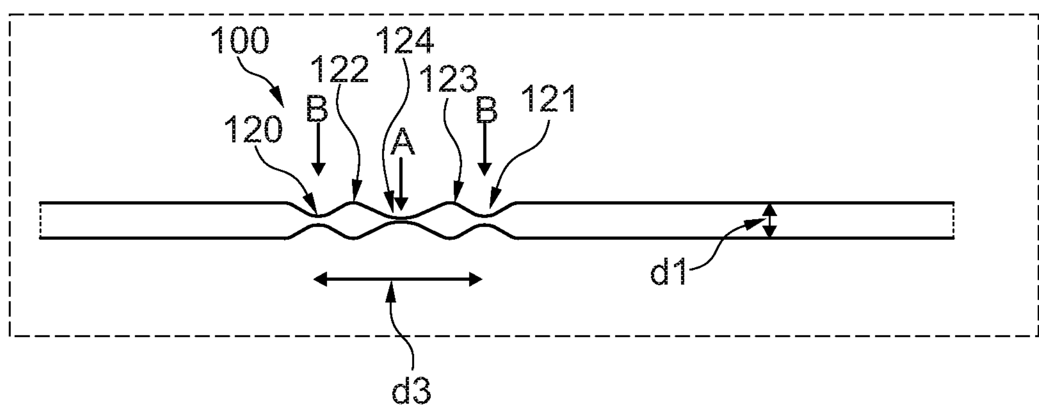
FIGS. 7 and 8 illustrate steps in a method of forming urinary catheter tip.
Figure 8:
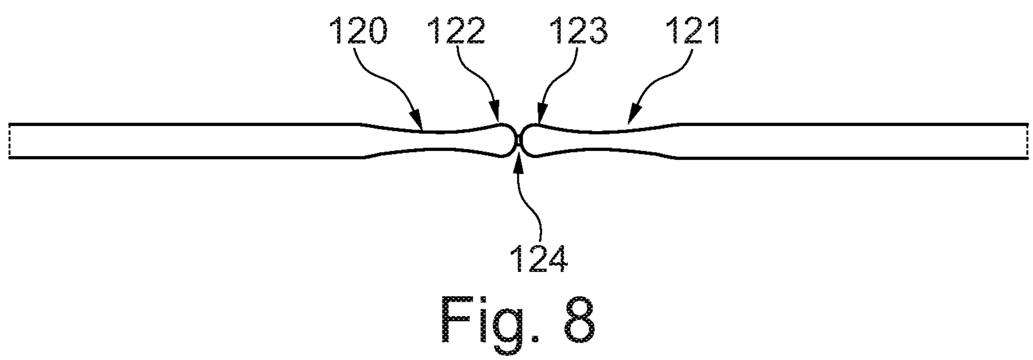

FIGS. 7 and 8 are similar to FIGS. 1 and 2 and illustrate an endless tubular object 100, which is obtained by an extrusion process. Like in FIGS. 1 and 2, the extruder is contemplated to be positioned to the left in the figures. The distal direction is defined as the direction towards the extruder and the proximal direction is defined as the direction away from the extruder. A first diameter d1 of the tubular object is indicated in FIG. 7.

In FIG. 7, it is indicated that the endless tubular object 100 has been indented twice in a first indentation 120 and a second indentation 121 spaced lengthwise apart by a third predetermined distance d3. Between the first indentation 120 and the second indentation 121, there is a first bulb 122 and a second bulb 123 distally thereof. Between the first and second bulb 122, 123, there is a break-indicator 124, which is configured for being cut through or being pulled apart, so as to divide the tubular object into two objects, each having a flex-tip.

Figure 9:
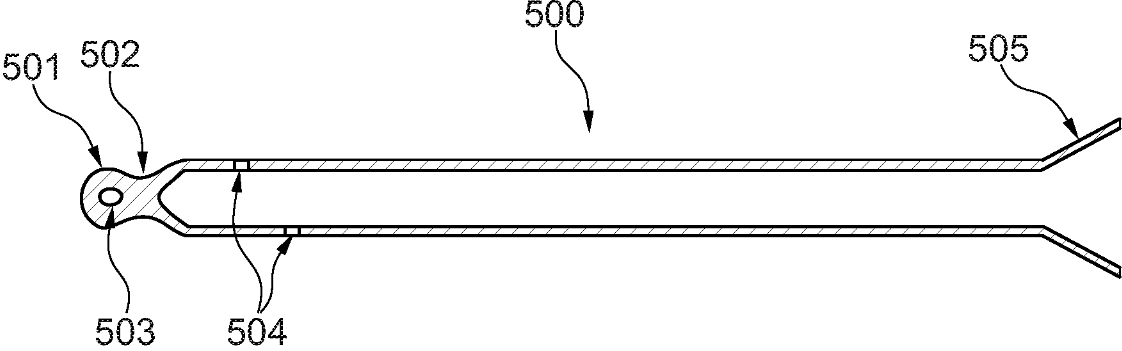
FIG. 9 illustrates a urinary catheter obtained by a method described herein.

FIG. 9 illustrates a urinary catheter 500 manufactured according to methods described herein. The catheter is provided with a bulb 501 in the proximal insertion end, the bulb 501 is followed distally by an indentation 502. As the figure illustrates, the bulb 501 may be hollow 503 and the indentation may be solid. The urinary catheter may be provided with several eyelets or drainage openings 504—only two are illustrated in the figure, however up to more than 100 may be provided. The urinary catheter 500 is provided with a connector 505 in the distal end.

Figures 10A, 10B, 10C:
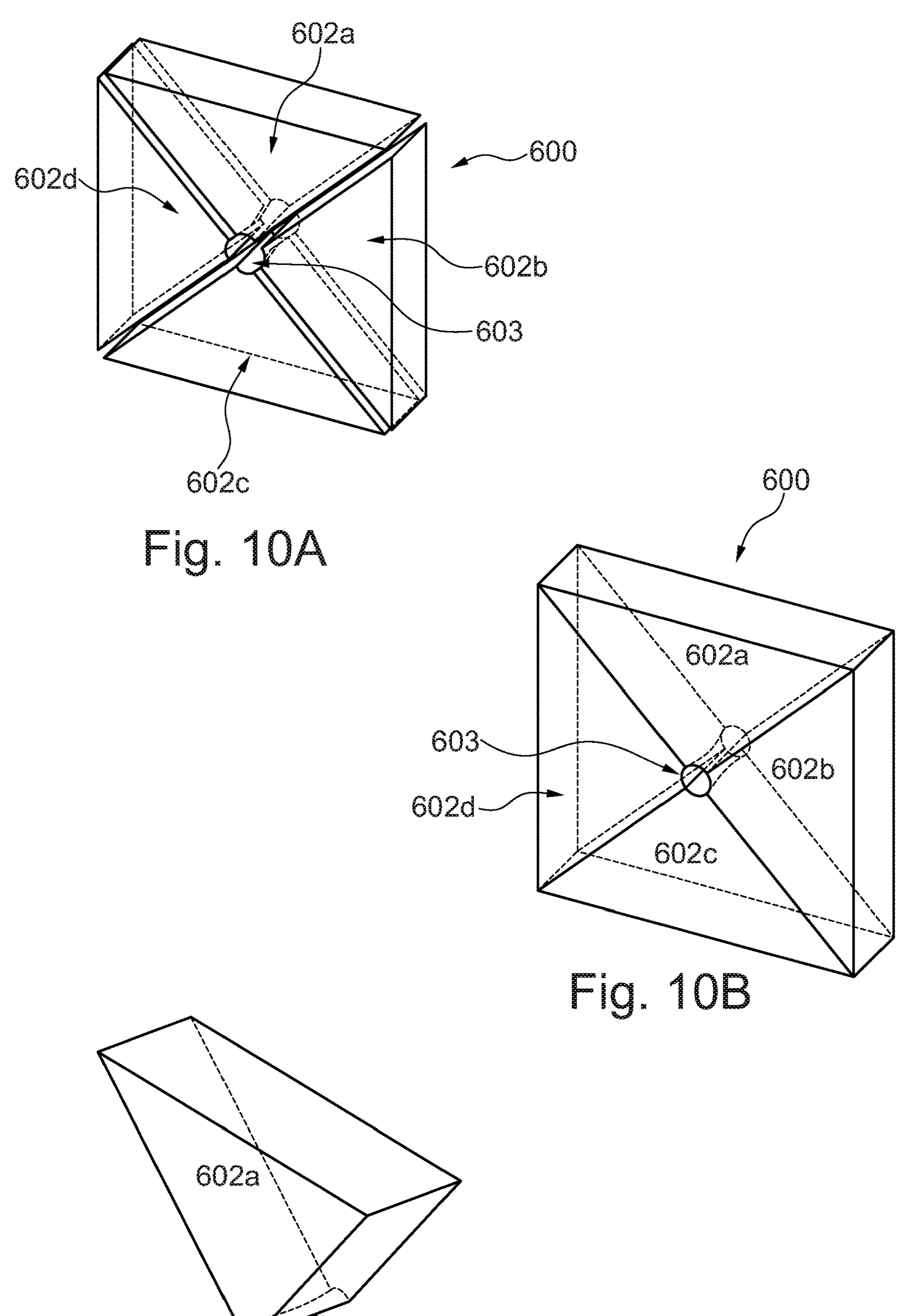
FIGS. 10A-10C illustrate a shaping tool, which can be used in methods described herein.

FIGS. 10A, 10B and 10C illustrate shaping tool 600, which may be used in a method of forming a urinary catheter tip or a method of manufacturing a urinary catheter described herein. The shaping tool 600 consists of four parts 602*a*, 602*b*, 602*c*, 602*d*, which in FIG. 10A is illustrated in an open position. In FIG. 10B, the shaping tool is illustrated in a closed position. The cavity 603, which is used to form the tip, is illustrated at the central portion of the shaping tool. FIG. 10C illustrates one of the four parts 602*a* in a larger scale.

Figure 11A:
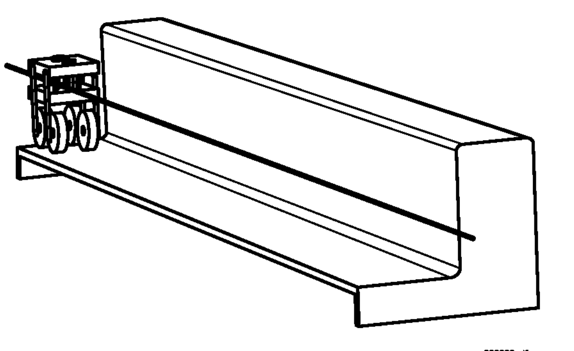
FIGS. 11A-11D illustrate steps in a manufacturing method described herein.
Figure 11B:
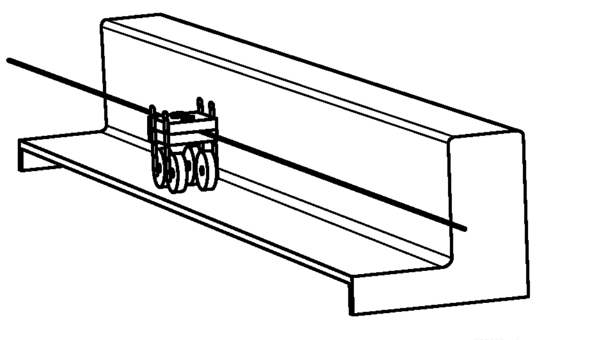
Figure 11C:
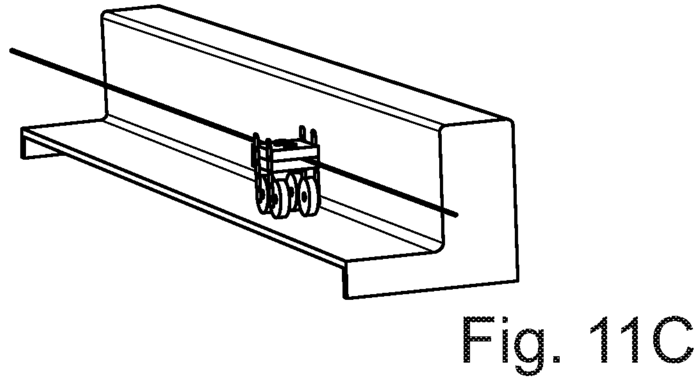
Figure 11D:
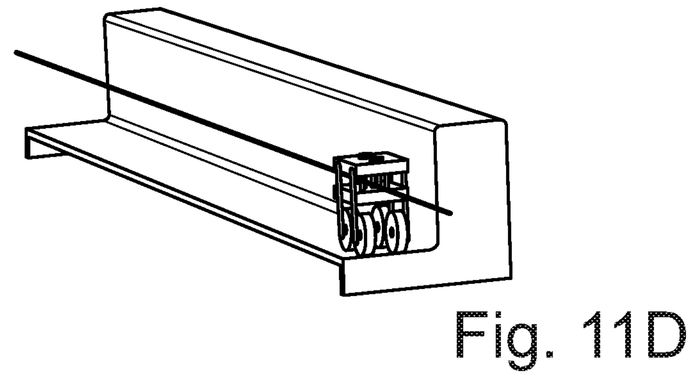

FIGS. 11A, 11B, 11C, 11D illustrate how the shaping tool 600 of FIGS. 10A, 10B, 10C can be used in the manufacturing system. The shaping tool 600 follows the tubular object 100 in the direction of manufacturing. In FIGS. 11A, 11B, 11C, the shaping tool is closed, whereas it is opened in FIG. 11D and can return to the other end of the manufacturing system ready for a new portion of a tubular object.

Embodiments, and features of the various exemplary embodiments described in this application, may be combined with each other ("mixed and matched"), unless specifically noted otherwise.

The invention claimed is:

1. A method of making a urinary catheter, the method comprising:

providing a tubular object made from plastic, the tubular object having a lumen located inside of a wall of the tubular object;

forming an indentation in the wall of the tubular object by pressing a shaping tool having a protrusion into the wall of the tubular object;

cutting the tubular object at a first predetermined distance proximal of the indentation and exposing the lumen and a proximal end of the wall of the tubular object;

cutting the tubular object at a second predetermined distance distal of the indentation and exposing the lumen and a distal end of the wall of the tubular object;

closing the proximal end of the tubular object and forming a rounded urinary catheter tip defining a proximal-most end of the tubular object;

providing eyelets in the tubular object distal of the indentation; and attaching a connector handle to the distal end of the wall of the tubular object.

2. The method of claim 1, wherein the closing the proximal end of the tubular object comprises heating and shaping the proximal end of the tubular object.

3. The method of claim 1, further comprising extruding the tubular object with an extruder and feeding the extruded tubular object into the shaping tool.

4. The method of claim 3, further comprising feeding the extruded tubular object into the shaping tool within 3 seconds after extruding the tubular object.

5. The method of claim 3, further comprising positioning the shaping tool at a distance between 3 cm and 10 cm from the extruder.

6. The method of claim 1, further comprising forming the indentation in the wall of the tubular object by pressing a heated shaping tool having a heated protrusion into the wall of the tubular object.

7. The method of claim 1, further comprising forming the indentation in the wall of the tubular object by pressing a heated shaping tool heated to a temperature of between 50° C. and 160° C. into the wall of the tubular object.

8. The method of claim 1, further comprising forming the indentation in the wall of the tubular object by inserting the tubular object between two opposing rotatable wheels and pressing a first protrusion on a first of the two opposing rotatable wheels into the wall of the tubular object and pressing a second protrusion on a second of the two opposing rotatable wheels into the wall of the tubular object.

9. The method of claim 8, further comprising symmetrically pressing the first protrusion on the first of the two opposing rotatable wheels into the wall of the tubular object while pressing the second protrusion on the second of the two opposing rotatable wheels into the wall of the tubular object.

10. The method of claim 8, further comprising pressing the first protrusion on the first of the two opposing rotatable wheels into the wall of the tubular object by rotating the first of the two opposing rotatable wheels at a first speed and symmetrically pressing the second protrusion on the second of the two opposing rotatable wheels into the wall of the tubular object by rotating the second of the two opposing rotatable wheels at the first speed.

11. The method of claim 8, wherein the first protrusion on the first of the two opposing rotatable wheels is offset in position relative to the second protrusion on the second of the two opposing rotatable wheels, the method further comprising pressing the first protrusion on the first of the two opposing rotatable wheels into the wall of the tubular object at a first linear location along the tubular object and non-symmetrically pressing the second protrusion on the second of the two opposing rotatable wheels into the wall of the tubular object at a different second linear location along the tubular object.

12. The method of claim 1, further comprising forming the indentation in the wall of the tubular object by inserting the tubular object into a continuous corrugator belt wherein the shaping tool comprises a number of shaping elements positioned along a face of the continuous corrugator belt.

13. The method of claim 12, further comprising forming the indentation in the wall of the tubular object by inserting the tubular object into the continuous corrugator belt wherein the shaping tool comprises a number of metal shaping elements spaced apart along the face of the continuous corrugator belt.

14. The method of claim 1, further comprising forming in sequence along the tubular object:

1) the indentation in the wall of the tubular object,
2) a first bulb on the wall of the tubular object,
3) a break-indicator forming in the wall of the tubular object,
4) a second bulb on the wall of the tubular object,
5) a second indentation pressed in the tubular object;

spacing the indentation away from the second indentation by a third predetermined distance;

cutting the tubular object at the break-indicator and forming a first tip end and a second tip end; and separating the first tip end away from the second tip end and forming a first urinary catheter having the first tip end and a second urinary catheter having the second tip end.

15. The method of claim 1, further comprising forming in sequence along the tubular object:

1) the indentation in the wall of the tubular object,
2) a first bulb on the wall of the tubular object,
3) a break-indicator forming in the wall of the tubular object,
4) a second bulb on the wall of the tubular object,
5) a second indentation pressed in the tubular object;

spacing the indentation away from the second indentation by a third predetermined distance;

pulling the tubular object in opposite directions at the break-indicator and separating a first tip end away from a second tip end and producing a first urinary catheter having the first tip end and a second urinary catheter having the second tip end.

* * * * *